(12) United States Patent
Staley

(10) Patent No.: US 10,702,689 B2
(45) Date of Patent: Jul. 7, 2020

(54) AUTO-STOP VENT PLUG

(71) Applicant: Becton, Dickinson and Company, Franklin Lakes, NJ (US)

(72) Inventor: Shaun Staley, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 223 days.

(21) Appl. No.: 15/078,563

(22) Filed: Mar. 23, 2016

(65) Prior Publication Data

US 2016/0279347 A1    Sep. 29, 2016

Related U.S. Application Data

(60) Provisional application No. 62/138,703, filed on Mar. 26, 2015.

(51) Int. Cl.
*A61M 39/20* (2006.01)
*A61M 5/38* (2006.01)

(52) U.S. Cl.
CPC ............ *A61M 39/20* (2013.01); *A61M 5/385* (2013.01); *A61M 5/38* (2013.01);
(Continued)

(58) Field of Classification Search
CPC ........ A61M 2039/205; A61M 2039/20; A61M 39/20; A61M 5/36; A61M 5/38;
(Continued)

(56) References Cited

U.S. PATENT DOCUMENTS 2,129,983 A    9/1938   Bacon
2,729,212 A    1/1956   Butler
(Continued)

FOREIGN PATENT DOCUMENTS

AU    771431 B2    3/2004
CA    2 460 251 A1    4/2003
(Continued)

OTHER PUBLICATIONS

Braun, Product Detail, the URL retrieved from http://www.bbraunoem-industrial.com/products/ details.cfm?prodid=B0843225&id-Caps &area=C, p. 1 (Apr. 12, 2005).
(Continued)

*Primary Examiner* — Kevin C Sirmons
*Assistant Examiner* — Tezita Z Watts
(74) *Attorney, Agent, or Firm* — Kirton & McConkie; Craig Metcalf; Kevin Stinger

(57) ABSTRACT

An intravenous delivery system may have a liquid source containing a liquid, tubing, and a vent cap. The tubing may be connected to the liquid source and the vent cap to convey liquid from the liquid source to the vent cap. The vent cap may have a vent that is substantially impermeable to the liquid and permeable to air, and therefore releases air from the liquid from the vent cap. The vent cap may also have a chamber in communication with the vent. The chamber may have a volume selected to enable the chamber to receive a quantity of liquid from the tubing in which the air, if entrained in the liquid, is likely to reside after the tubing has been primed with the liquid.

9 Claims, 4 Drawing Sheets

(52) U.S. Cl.
CPC ............... *A61M 2039/205* (2013.01); *A61M 2205/7527* (2013.01); *A61M 2205/7536* (2013.01)

(58) Field of Classification Search
CPC ............... A61M 5/385; A61M 5/1411; A61M 2205/7527; A61M 2205/7536
See application file for complete search history.

(56) References Cited

U.S. PATENT DOCUMENTS

| | | | |
|---|---|---|---|
| 2,954,028 A | 9/1960 | Smith | |
| 3,030,954 A | 4/1962 | Thornton, Jr. | |
| 3,390,677 A | 7/1968 | Razimbaud | |
| 3,520,416 A | 7/1970 | Keedwell | |
| 3,557,786 A | 1/1971 | Barr, Sr. et al. | |
| 3,631,654 A | 1/1972 | Riely et al. | |
| 3,722,697 A | 3/1973 | Burke et al. | |
| 3,744,492 A | 7/1973 | Leibinsohn | |
| 3,756,233 A | 9/1973 | Goldowsky | |
| 3,782,083 A | 1/1974 | Rosenberg | |
| 3,806,386 A | 4/1974 | Burke et al. | |
| 3,931,818 A | 1/1976 | Goldowsky | |
| 3,960,149 A | 6/1976 | Bujan | |
| 4,013,072 A | 3/1977 | Jess | |
| 4,034,754 A * | 7/1977 | Virag | A61M 5/36 604/81 |
| 4,066,556 A | 1/1978 | Vaillancourt | |
| 4,113,627 A | 9/1978 | Leason | |
| 4,121,584 A | 10/1978 | Turner et al. | |
| 4,170,056 A | 10/1979 | Meyst et al. | |
| 4,173,222 A | 11/1979 | Muetterties | |
| 4,198,971 A | 4/1980 | Noiles | |
| 4,200,095 A | 4/1980 | Reti | |
| 4,227,527 A * | 10/1980 | De Frank | A61M 39/20 604/263 |
| 4,243,032 A | 1/1981 | Howell | |
| 4,248,223 A | 2/1981 | Turner et al. | |
| 4,269,222 A | 5/1981 | Palti | |
| 4,276,170 A | 6/1981 | Vaillancourt | |
| 4,319,996 A | 3/1982 | Vincent et al. | |
| 4,372,304 A | 2/1983 | Avakian et al. | |
| 4,384,578 A | 5/1983 | Winkler | |
| 4,406,042 A | 9/1983 | McPhee | |
| 4,413,990 A | 11/1983 | Mittleman | |
| 4,428,743 A | 1/1984 | Heck | |
| 4,465,479 A | 8/1984 | Meisch | |
| 4,521,212 A | 6/1985 | Ruschke | |
| 4,548,600 A | 10/1985 | Ruschke | |
| 4,571,244 A | 2/1986 | Knighton | |
| 4,583,979 A | 4/1986 | Palti | |
| 4,589,171 A | 5/1986 | McGill | |
| 4,601,712 A | 7/1986 | Cole et al. | |
| 4,610,781 A | 9/1986 | Bilstad et al. | |
| 4,615,694 A | 10/1986 | Raines | |
| 4,625,494 A | 12/1986 | Iwatschenko et al. | |
| 4,634,426 A | 1/1987 | Kamen | |
| 4,675,017 A | 6/1987 | Sato | |
| 4,681,563 A | 7/1987 | Deckert et al. | |
| 4,685,912 A | 8/1987 | Jones | |
| 4,795,429 A | 1/1989 | Feldstein | |
| 4,812,293 A | 3/1989 | McLaurin et al. | |
| 4,820,281 A | 4/1989 | Lawler, Jr. | |
| 4,842,588 A | 6/1989 | Jones | |
| 4,952,210 A | 8/1990 | Alchas | |
| 4,997,149 A | 3/1991 | Koch | |
| 5,102,400 A | 4/1992 | Leibinsohn | |
| 5,131,537 A | 7/1992 | Gonzales | |
| 5,188,588 A | 2/1993 | Schoendorfer et al. | |
| 5,195,987 A | 3/1993 | Karpiak | |
| 5,308,314 A | 5/1994 | Fukui et al. | |
| 5,308,333 A | 5/1994 | Skakoon | |
| 5,309,604 A | 5/1994 | Poulsen | |
| 5,389,082 A | 2/1995 | Baugues et al. | |
| 5,419,770 A | 5/1995 | Crass et al. | |
| 5,423,346 A | 6/1995 | Daoud | |
| 5,423,769 A | 6/1995 | Jonkman et al. | |
| 5,435,448 A | 7/1995 | Kempen | |
| 5,489,385 A | 2/1996 | Raabe et al. | |
| 5,542,160 A | 8/1996 | Amdt | |
| 5,681,294 A | 10/1997 | Osborne et al. | |
| 5,709,653 A | 1/1998 | Leone | |
| 5,735,826 A | 4/1998 | Richmond | |
| 5,776,109 A | 7/1998 | Urrutia | |
| 5,779,674 A | 7/1998 | Ford | |
| 5,836,923 A | 11/1998 | Mayer | |
| 5,851,202 A | 12/1998 | Carlsson | |
| 5,891,096 A | 4/1999 | Hyun et al. | |
| 5,899,665 A | 5/1999 | Makino et al. | |
| 5,902,281 A | 5/1999 | Kraus et al. | |
| 5,906,598 A | 5/1999 | Giesler et al. | |
| 6,015,119 A | 1/2000 | Starchevich | |
| 6,099,512 A | 8/2000 | Urrutia | |
| 6,103,119 A | 8/2000 | Clements et al. | |
| 6,106,504 A | 8/2000 | Urrutia | |
| 6,149,631 A | 11/2000 | Haydel, Jr. | |
| 6,213,986 B1 | 4/2001 | Darling, Jr. | |
| 6,224,578 B1 | 5/2001 | Davis et al. | |
| 6,261,267 B1 | 7/2001 | Chen | |
| 6,283,945 B1 | 9/2001 | Bierman | |
| 6,336,916 B1 | 1/2002 | Bormann et al. | |
| 6,503,225 B1 * | 1/2003 | Kirsch | A61M 1/3627 422/48 |
| RE38,145 E | 6/2003 | Lynn | |
| D479,328 S | 9/2003 | Reynolds et al. | |
| 6,685,668 B1 | 2/2004 | Cho et al. | |
| 6,833,488 B2 | 12/2004 | Bucevschi et al. | |
| 7,160,087 B2 | 1/2007 | Fathallah et al. | |
| 7,255,680 B1 | 8/2007 | Gharib | |
| 7,722,577 B2 | 5/2010 | Miner | |
| 7,892,204 B2 | 2/2011 | Kraus | |
| 8,282,046 B2 | 10/2012 | Harding et al. | |
| 8,523,829 B2 | 9/2013 | Miner et al. | |
| 9,435,455 B2 | 9/2016 | Peret et al. | |
| 9,452,255 B2 | 9/2016 | Tieck et al. | |
| 2002/0156431 A1 | 10/2002 | Feith et al. | |
| 2003/0048185 A1 | 3/2003 | Citrenhaum et al. | |
| 2003/0220616 A1 | 11/2003 | Kraus | |
| 2004/0011749 A1 | 1/2004 | Hutchinson et al. | |
| 2004/0254542 A1 | 12/2004 | Sacco | |
| 2005/0059926 A1 | 3/2005 | Sage, Jr. et al. | |
| 2005/0171491 A1 | 8/2005 | Minh Miner et al. | |
| 2005/0249885 A1 | 11/2005 | Weis et al. | |
| 2005/0273062 A1 | 12/2005 | Franksson et al. | |
| 2006/0188407 A1 * | 8/2006 | Gable | A61B 5/0084 604/19 |
| 2006/0283544 A1 | 12/2006 | Mori et al. | |
| 2007/0156118 A1 * | 7/2007 | Ramsey | A61M 39/20 604/533 |
| 2008/0097333 A1 | 4/2008 | Henning | |
| 2009/0088710 A1 * | 4/2009 | Hoffman | A61M 1/0049 604/323 |
| 2009/0093774 A1 | 4/2009 | Wang et al. | |
| 2011/0276010 A1 * | 11/2011 | Davis | A61M 5/1411 604/244 |
| 2012/0171403 A1 | 7/2012 | Dodge | |
| 2013/0224866 A1 | 8/2013 | Lurvey et al. | |
| 2013/0338588 A1 | 12/2013 | Grimm et al. | |
| 2013/0345658 A1 * | 12/2013 | Browne | A61M 5/16831 604/500 |
| 2014/0228806 A1 | 8/2014 | Alisantoso et al. | |
| 2016/0339229 A1 | 11/2016 | Hung et al. | |

FOREIGN PATENT DOCUMENTS

| | | |
|---|---|---|
| CN | S48-63591 | 9/1973 |
| CN | S61-206445 | 9/1986 |
| CN | 201 088 751 Y | 7/2008 |
| CN | 101 732 767 A | 6/2010 |
| CN | 102716533 | 10/2012 |
| CN | 102883763 | 1/2013 |
| CN | 203 107 819 U | 8/2013 |
| CN | 203 379 419 U | 1/2014 |

(56) References Cited

FOREIGN PATENT DOCUMENTS

| | | |
|---|---|---|
| CN | 104274487 | 1/2015 |
| DE | 41 42 625 A1 | 4/1993 |
| DE | 196 22 050 A1 | 12/1997 |
| EP | 0 001 114 A2 | 3/1979 |
| EP | 0 195 310 A1 | 9/1986 |
| EP | 0 229 354 A2 | 7/1987 |
| EP | 0 788 824 A3 | 11/1998 |
| EP | 1 181 065 B1 | 7/2003 |
| EP | 2 500 051 A1 | 9/2012 |
| FR | 2 160 821 A1 | 7/1973 |
| GB | 2 044 620 A | 10/1980 |
| JP | S50-63795 | 6/1975 |
| JP | S55-45245 | 11/1980 |
| JP | S62-170258 | 7/1987 |
| JP | S63-212371 | 9/1988 |
| JP | H10-127778 A | 5/1998 |
| JP | H11-502771 | 3/1999 |
| JP | 2000-014745 A | 1/2000 |
| JP | 2000-229126 A | 8/2000 |
| JP | 2002522123 | 7/2002 |
| JP | 2008500879 | 1/2008 |
| JP | 2009522048 | 6/2009 |
| JP | 2009-219798 | 10/2009 |
| JP | 2013505156 | 2/2013 |
| JP | 2013525065 | 6/2013 |
| WO | 96/29104 A1 | 9/1996 |
| WO | 99/22787 A1 | 5/1999 |
| WO | 00/66200 A1 | 11/2000 |
| WO | 01/41844 A1 | 6/2001 |
| WO | 03/028525 A2 | 4/2003 |
| WO | 2005/104776 A2 | 11/2005 |
| WO | 2005/118051 A2 | 12/2005 |
| WO | 2006/083359 A2 | 8/2006 |
| WO | 2007/079049 A2 | 7/2007 |
| WO | 2008/027157 A1 | 3/2008 |
| WO | WO-2008058132 A2 * | 5/2008 ............ A61M 39/20 |
| WO | 2009/046182 A1 | 4/2009 |
| WO | 2010/030602 | 3/2010 |
| WO | 2010/030602 A1 | 3/2010 |
| WO | 2011/139517 | 11/2011 |
| WO | 2011/139517 A1 | 11/2011 |
| WO | 2013/070337 A1 | 5/2013 |
| WO | 2013/188103 A1 | 12/2013 |

OTHER PUBLICATIONS

Shift Labs, DripAssist Infusion Rate Monitor, http://www.shiftlabs.com/dripassist-human-health, pp. 1-5, Apr. 3, 2017.
Brown, et al.: "Non-contact laser sealing of thin polyester food packaing films", Optics and Lasers Engineering, Elsevier, Amsterdam, NL, vol. 50, No. 10, Apr. 2, 2012, pp. 1466-1473, XP028500061.
Braun, Product Detail, http://www.bbraunoem-industrial.com/products/details.cfm?prodid=B0843225&id-Caps&area=C, p. 1 (Apr. 12, 2005).

* cited by examiner

AUTO-STOP VENT PLUG

RELATED APPLICATIONS

This application claims priority to U.S. Provisional Patent Application Ser. No. 62/138,703, filed Mar. 26, 2015, and entitled IMPROVED AUTO-STOP VENT PLUG, which is incorporated herein in its entirety.

BACKGROUND

The present invention is generally directed to systems and methods for intravenous ("IV") delivery, by which fluids can be administered directly to the vascular system of a patient. More particularly, the present invention is directed to a vent cap that can be included within an intravenous delivery system set to facilitate venting of air from the intravenous delivery system. An intravenous delivery system according to the invention is used broadly herein to describe components used to deliver the fluid to the patient, for use in arterial, intravenous, intravascular, peritoneal, and/or nonvascular administration of fluid. Of course, one of skill in the art may use an intravenous delivery system to administer fluids to other locations within a patient's body.

One common method of administering fluids into a patient's blood flow is through an intravenous delivery system. In many common implementations, an intravenous delivery system may include a liquid source such as a liquid bag, a drip chamber used to determine the flow rate of fluid from the liquid bag, tubing for providing a connection between the liquid bag and the patient, and an intravenous access unit, such as a catheter that may be positioned intravenously in a patient. An intravenous delivery system may also include a Y-connector that allows for the piggybacking of intravenous delivery systems and for the administration of medicine from a syringe into the tubing of the intravenous delivery system.

It is a generally good practice to remove air from intravenous delivery systems that access a patient's blood flow. While this concern is critical when accessing arterial blood, it is also a concern when accessing the venous side. Specifically, if air bubbles are allowed to enter a patient's blood stream while receiving the intravenous administration of fluids, the air bubbles can form an air embolism and cause serious injury to a patient.

Normally, in a majority of adults, the right atrium and the left atrium are completely separated from each other so that the blood and air bubbles are moved from the right atrium, to the right ventricle, and then to the lungs where the air bubbles may be safely vented. The bubble free blood is then returned to the left atrium, where the blood is moved to the left ventricle and then sent throughout the body.

However, in infants and in a small portion of the adult population, the right atrium and left atrium are not completely separated. Consequently, air bubbles can move directly from the right atrium into the left atrium and then be dispersed throughout the body. As a result, these air bubbles may cause strokes, tissue damage, and/or death. Therefore, it is important to prevent air bubbles from entering a patient's blood stream.

In spite of the importance of removing air bubbles while priming an intravenous delivery system for use in the intravenous administration of fluids, the complete removal of air bubbles can be a time consuming process. The process may also lead to contamination of the intravenous delivery system by inadvertently touching a sterile end of the intravenous delivery system. Typically, when an intravenous delivery system is primed, a clamp is closed to prevent fluid from moving from a drip chamber through the tubing. The intravenous delivery system may then be attached to an IV bag or bottle. Once attached, the drip chamber, which is typically made of a clear flexible plastic, may be squeezed to draw the fluid out of the IV bag or bottle and into the drip chamber. The drip chamber may be allowed to fill about ¼ to ½ full when the clamp is opened to allow fluid to flow through the tube to an end of the intravenous delivery system.

This initial process, however, typically traps air in tubing which must be removed. For example, the flow of the fluid through the tubing of the intravenous delivery system may be turbulent and can entrap air within the tube as the boundary layer between the fluid and the tubing is sheared. The flow rate out of the drip chamber may be higher than the flow rate of fluid entering the drip chamber. This can cause a bubble ladder to form as air is sucked from the drip chamber into the tubing.

Additionally, air bubbles may be generated as drops of fluid strike the surface of the pool of fluid within the drip chamber. These air bubbles can be pulled into the tubing of the IV set from the drip chamber. This problem may be aggravated in pediatric applications where the drip orifice may be smaller, which may result in increased turbulence.

To remove air bubbles from the intravenous delivery system, fluid from the IV bag or bottle may be allowed to flow through the tubing while an attendant taps the tubing to encourage the air bubbles out the end of the intravenous delivery system. As the fluid is allowed to flow out of the intravenous delivery system to clear air bubbles from the tubing, the fluid may be allowed to flow into a waste basket or other receptacle. During this procedure, the end of the tubing may contact the waste basket or be touched by the attendant and thus, become contaminated. An additional shortcoming of this debubbling process is that it requires attention and time that could have been used to perform other tasks that may be valuable to the patient.

Another debubbling method is to directly remove air bubbles from the intravenous delivery system. More specifically, if the intravenous delivery system includes a Y-connector, air bubbles may be removed at the Y-connector by a syringe. This method still requires additional time and attention, and may also carry risk of contamination of the liquid to be delivered.

To address the difficulties of removing bubbles from an intravenous delivery system, various prior art intravenous delivery systems have employed a membrane for filtering air from the fluid as it flows through the intravenous delivery system. For example, oftentimes a membrane may be placed in the bottom of the drip chamber so that fluid flowing out of the drip chamber must pass through the membrane. The membrane can be configured to allow the passage of fluid while blocking the passage of air. In this way, bubbles are prevented from passing into the tubing leading to the patient. Similarly, a membrane can be included in the connector that couples the tubing to a catheter to block any air present in the tubing from passing into the patient's vasculature.

Additionally or alternatively, some known intravenous delivery systems utilize a vent cap, which may be coupled to the free end of the tubing prior to attachment of the catheter. Such vent caps are generally intended to vent air out of the intravenous delivery system. However, known vent caps generally accommodate only a very small quantity of the liquid. Air may be entrained in the liquid, and may remain trapped in the tubing when the intravenous delivery system is fully primed.

Thus, such vent caps are not always effective at venting air. In some instances, the clinician must take steps to manually release the air, which requires additional time and attention, and may also carry risk of contamination of the liquid, as detailed above.

Further, some known vent caps have valves that help retain liquid within the vent cap after detachment of the vent cap from the tubing. Such valves are often complex structures, and in many instances, such valves require the presence of corresponding hardware on the tubing to open the valve when the vent cap is attached to the tubing. Accordingly, such valves add to the complexity and cost of known intravenous delivery systems, and may also add failure points that can cause unexpected leakage in the event of improper attachment, manufacturing defects, and/or the like.

BRIEF SUMMARY OF THE INVENTION

Embodiments of the present invention are generally directed to an intravenous delivery system with a vent cap that provides enhanced air venting. The intravenous delivery system may have a liquid source containing a liquid to be delivered to a patient, tubing, and the vent cap. The tubing may have a first end connectable to the liquid source, and a second end connectable to the vent cap.

The vent cap may have a proximal end connectable to the distal end of the tubing to receive the liquid, and a distal end having a vent that is substantially impermeable to the liquid and substantially permeable to air. Further, the vent cap may have a chamber wall that defines a chamber that receives the liquid from the proximal end. The chamber may have a volume selected to enable the chamber to receive a quantity of liquid from the tubing in which the air, if entrained in the liquid, is likely to reside after the tubing has been primed sufficiently to advance the liquid through the second end of the tubing.

The desired volume of the chamber may be determined by the equation $V=\pi r^2 l$, where V is the volume, r is a radius of an interior of the tubing, and l is a length of tubing within which the air, if present in the liquid, is likely to reside after the tubing has been primed. In some embodiments, the length referenced in the equation may range from 2 inches to greater than 5 inches. The volume may range from 0.3 milliliters to greater than 1.0 milliliters.

The chamber wall may have a generally tubular shape with an interior diameter that ranges from 7 millimeters to 15 millimeters, a length that ranges from 5 millimeters to 15 millimeters. The geometry of the chamber does not need to be tubular and can be cubic, frustoconical, etc. The proximal end of the vent cap may have a vent cap luer lock that mates with a tubing luer lock of the second end of the tubing. The chamber wall may be shaped to have a proximal flare that provides the chamber wall with an interior diameter greater than the largest interior diameter of the vent cap luer lock.

The vent cap may be detachably connectable to the second end of the tubing, for example, through the use of the vent cap luer lock and the tubing luer lock referenced above. The vent cap may be configured to retain substantially all of the liquid it has received after detachment of the vent cap from the tubing, without requiring the presence of a valve within the vent cap. More specifically, the chamber wall may be shaped to define an orifice adjacent to the chamber. The orifice may be sized to substantially prevent liquid outflow from the chamber. Additionally or alternatively, the orifice may be covered with a hydrophilic membrane that prevents outflow of the liquid. The vent may have a hydrophobic membrane that facilitates release of the air from the vent cap, while retaining the liquid.

The intravenous delivery system may also have other components. Such components may include a drip unit that receives the liquid from the liquid source and delivers it to the tubing, and/or an intravenous access unit that is connectable to the second end of the tubing to deliver the liquid to the patient.

According to one method, an intravenous delivery system may be prepared for use by, first, connecting the various components of the intravenous delivery system together, as indicated previously. This may entail connecting the first end of the tubing to the liquid source and/or the drip chamber, and/or connecting the second end of the tubing to the vent cap. The second end of the tubing may be connected to the vent cap via a vent cap luer lock and a tubing luer lock, as indicated previously.

The intravenous delivery system may then be primed by gravity feeding liquid from the liquid source to the vent cap through the tubing. In response to priming the intravenous delivery system, the vent cap may receive a quantity of the liquid from the tubing in which air, if entrained in the liquid, is likely to reside after the tubing has been primed sufficiently to advance the liquid through the second end of the tubing. In response to receipt of the quantity of liquid within the vent cap, the air may be vented out of the vent cap.

After the air has been vented out of the vent cap, the vent cap may be detached from the second end of the tubing. In some embodiments, this may entail retaining substantially all of the quantity of liquid within the vent cap, without requiring the presence of a valve within the vent cap. The intravenous access unit may then be connected to the second end of the tubing. The intravenous access unit may then be ready for use to access the patient's vascular system to deliver the liquid to the patient.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention can be understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Moreover, the Figures may show simplified or partial views, and the dimensions of elements in the Figures may be exaggerated or otherwise not in proportion for clarity. In addition, the singular forms "a," "an," and "the" include plural referents unless the context clearly dictates otherwise. Thus, for example, reference to a terminal includes reference to one or more terminals. In addition, where reference is made to a list of elements (e.g., elements a, b, c), such reference is intended to include any one of the listed elements by itself, any combination of less than all of the listed elements, and/or a combination of all of the listed elements.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As used herein, the term "proximal", "top", "up" or "upwardly" refers to a location on the device that is closest to the clinician using the device and farthest from the patient in connection with whom the device is used when the device is used in its normal operation. Conversely, the term "distal", "bottom", "down" or "downwardly" refers to a location on the device that is farthest from the clinician using the device and closest to the patient in connection with whom the device is used when the device is used in its normal operation.

As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device.

Figure 1:
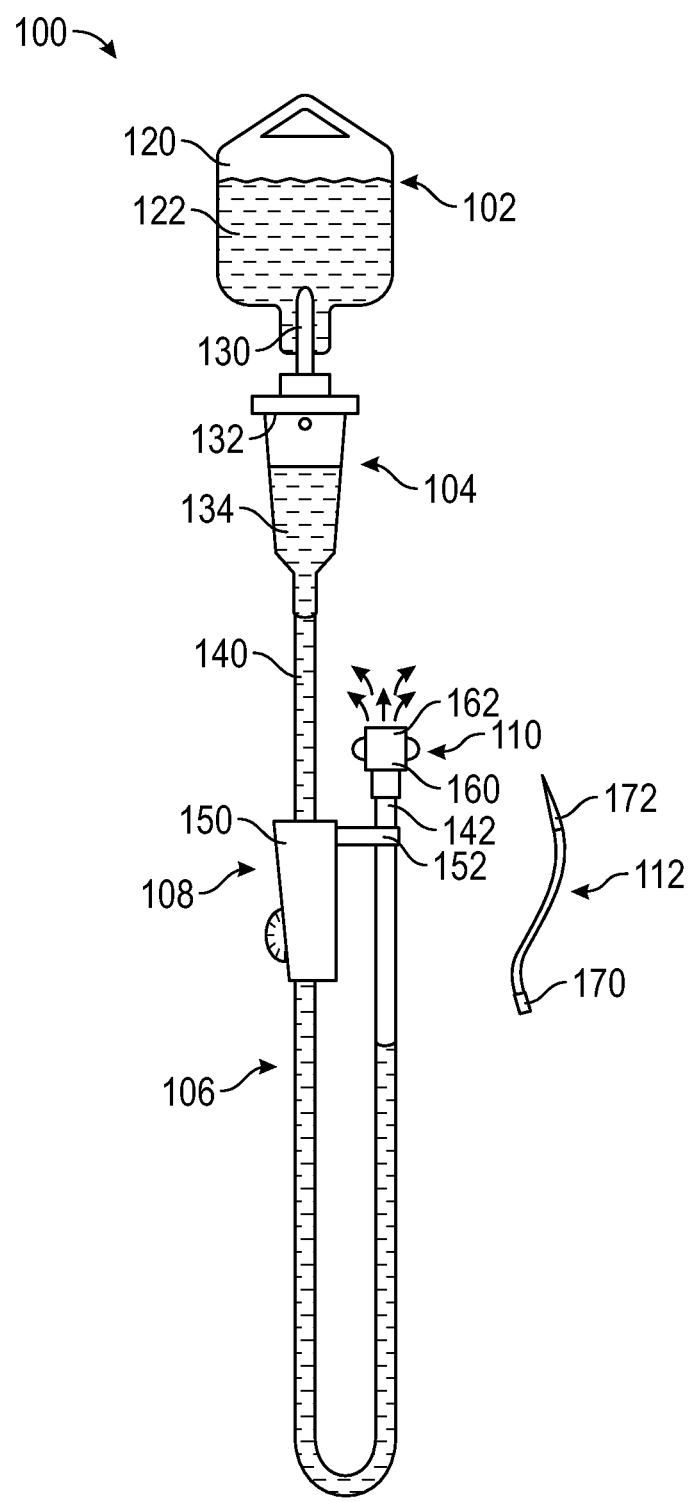
FIG. 1 is a front elevation view of an intravenous delivery system according to one embodiment.

Referring to FIG. 1, a front elevation view illustrates an intravenous delivery system 100 according to one embodiment. As shown, the intravenous delivery system 100 may have a number of components, which may include a liquid source 102, a drip unit 104, tubing 106 a retention unit 108, a vent cap 110, and an intravenous access unit 112. The manner in which these components are illustrated in FIG. 1 is merely exemplary; those of skill in the art will recognize that a wide variety of intravenous delivery systems exist. Thus, the various components the intravenous delivery system 100 may be omitted, replaced, and/or supplemented with components different from those illustrated.

The liquid source 102 may have a container containing a liquid 122 to be delivered intravenously to a patient. The liquid source 102 may, for example, have a bag 120, which may be formed of a translucent, flexible polymer or the like. The bag 120 may be shaped to contain the liquid 122.

The drip unit 104 may be designed to receive the liquid 122 from the bag 120 in a measured rate, for example, as a series of drips occurring at a predictable, consistent rate. The drip unit 104 may be positioned below the bag 120 so as to receive the liquid 122 via gravity feed. The drip unit 104 may have a receiving device 130 that receives the liquid 122 from the liquid source 102, a drip feature 132 that determines the rate at which the liquid 122 is received by the drip unit 104, and a drip chamber 134 in which the liquid 122 is collected.

The tubing 106 may be standard medical grade tubing. The tubing 106 may be formed of a flexible, translucent material such as a silicone rubber. The tubing 106 may have a first end 140 and a second end 142. The first end 140 may be coupled to the drip unit 104, and the second end 142 may be coupled to the vent cap 110, such that the liquid 122 flows from the drip unit 104 to the vent cap 110, through the tubing 106.

The retention unit 108 may be used to retain various other components of the intravenous delivery system 100. As shown, the retention unit 108 may have a main body 150 and an extension 152. Generally, the tubing 106 may be connected to the main body 150 proximate the first end 140, and to the extension 152 proximate the second end 142. Various racks, brackets, and/or other features may be used in addition to or in place of the retention unit 108.

The vent cap 110 may have a proximal end 160 and a distal end 162. The proximal end 160 may be coupled to the second end 142 of the tubing 106. The distal end 162 may be exposed to the ambient air so that air from within the vent cap 110 can be vented from the intravenous delivery system 100 through the distal end 162.

The intravenous access unit 112 may be used to supply the liquid 122 to the vascular system of the patient. The intravenous access unit 112 may have a first end 170 and an access end 172. The first end 170 may be connectable to the second end 142 of the tubing 106 in place of the vent cap 110. Thus, when the intravenous delivery system 100 is fully primed, the intravenous access unit 112 may be coupled to the second end 142 of the tubing 106 in place of the vent cap 110. In alternative embodiments (not shown), various connectors such as Y-adapters may be used to connect the first end 170 of the intravenous access unit 112 to the tubing 106 without detaching the vent cap 110 from the second end 142 of the tubing 106.

The intravenous delivery system 100 may be primed by connecting the components (except for the intravenous access unit 112) together as illustrated in FIG. 1, and then allowing the liquid 122 to gravity feed through the drip unit 104 and the tubing 106 into the vent cap 110. If desired, the drip unit 104 may be squeezed or otherwise pressurized to expedite flow of the liquid 122 through the tubing 106.

As the liquid 122 flows through the tubing 106, air may become entrained in the liquid 122. This air may move from the first end 140 of the tubing 106, toward the second end 142 of the tubing 106, along with the column of liquid 122. This entrained air may gather into bubbles proximate the second end 142 of the tubing 106. The vent cap 110 may be designed to receive a volume of the liquid 122 sufficient to permit passage of such air bubbles into the vent cap 110, so that they can be vented from the intravenous delivery system 100 through the distal end 162 of the vent cap 110. The manner in which the vent cap 110 accomplishes this will be shown and described in connection with FIG. 2.

Figure 2:
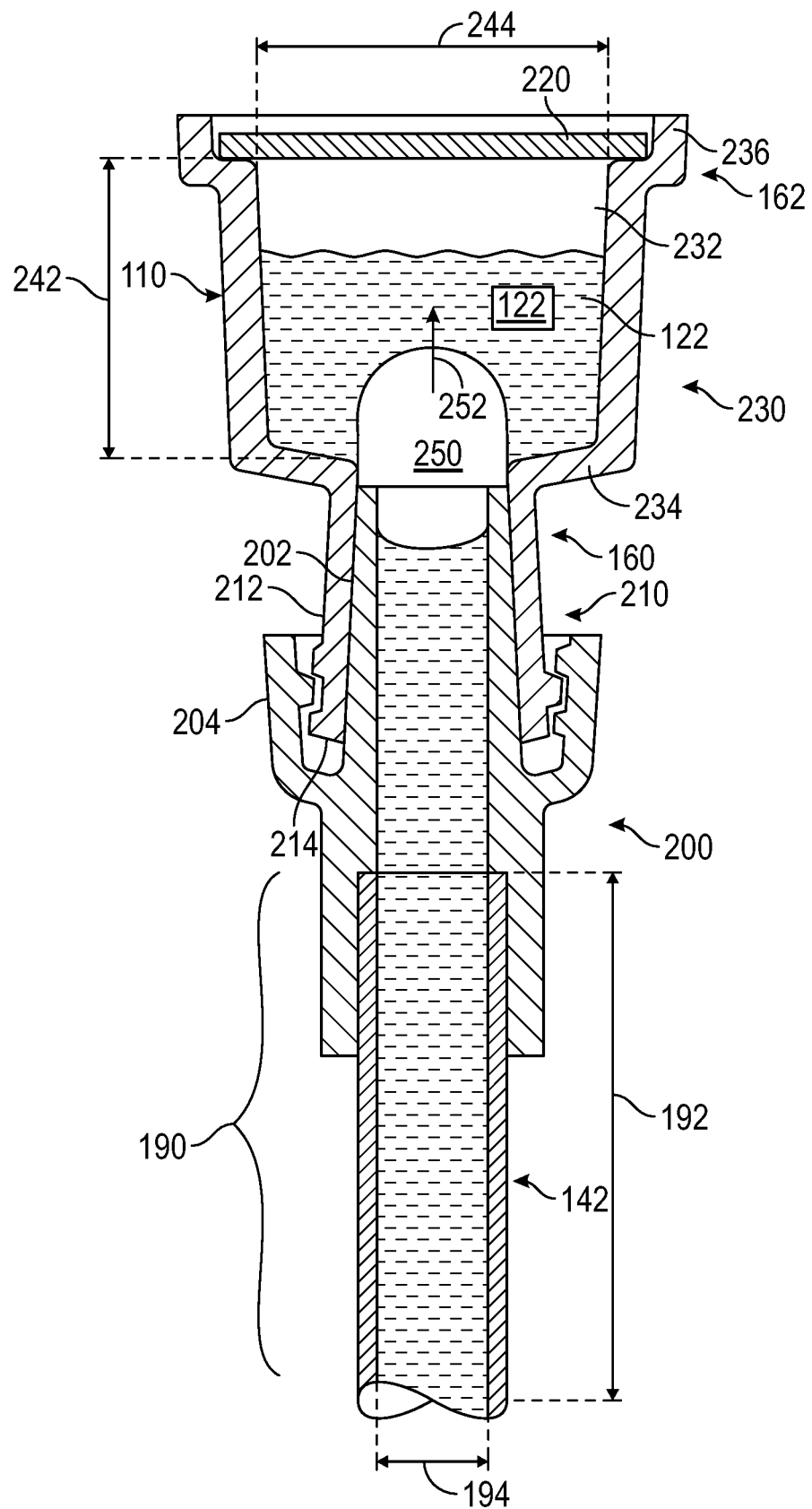
FIG. 2 is a front elevation, section view of a portion of the tubing and the vent cap of the intravenous delivery system of FIG. 1.

Referring to FIG. 2, a front elevation, section view illustrates a portion of the tubing 106 and the vent cap 110 of the intravenous delivery system 100 of FIG. 1. As shown, the second end 142 of the tubing 106 may have an air-carrying portion 190 in which air, if present in the liquid 122, tends to reside until vented from the intravenous delivery system 100. The air-carrying portion 190 may have a volume with a generally cylindrical shape defined by and contained within the generally tubular shape of the tubing 106. Thus, the air-carrying portion 190 may have a length 192 and a diameter, which may be an interior diameter 194 of the second end 142 of the tubing 106. The volume of the air-carrying portion 190 may be determined by the equation $V_t = \pi r_t^2 l_t$, where $l_t$ is the length 192 of the air-carrying portion 190, and $r_t$ is the radius of the air-carrying portion 190, which is half of the interior diameter 194 of the second end 142 of the tubing 106.

According to one example, the interior diameter 194 of the second end 142 of the tubing 106 may be about 2.8 millimeters. The length 192 may fall within the range of 2 inches to 15 inches. More specifically, the length 192 may fall within the range of 3 inches to 4.5 inches. Yet more specifically, the length 192 may be about 4 inches. It has been observed that, in prior art intravenous delivery systems that have problems with residual air after priming, air bubbles tend to reside within the segment of tubing adjacent to the vent cap 110, within about 4 inches of the vent cap 110. Setting the length 192 of the air-carrying portion 190 equal to approximately 4 inches reflects this observation. The volume $V_t$ of the air-carrying portion 190 may fall within the range of 0.3 milliliters to 2.7 milliliters. More specifically, the volume $V_t$ of the air-carrying portion 190 may fall within the range of 0.47 milliliters to 0.7 milliliters. Yet more specifically, the volume $V_t$ of the air-carrying portion 190 may be about 0.625 milliliters.

The second end 142 of the tubing 106 may have a connector designed to facilitate detachable coupling of the second end 142 to the proximal end 160 of the vent cap 110. Various types of connectors may be used. In some examples, luer type connectors of a type known in the art may be used. As embodied in FIG. 2, the connector may take the form of a tubing luer lock 200, which may be secured to the tubing material of the second end 142. The tubing luer lock 200 may have a male tapered fitting 202 that extends distally, toward the vent cap 110. The tubing luer lock 200 may further have a female threaded interface 204.

Similarly, the proximal end 160 of the vent cap 110 may have a vent cap luer lock 210 designed to mate with the tubing luer lock 200 such that the vent cap 110 may be easily and detachably coupled to the second end 142 of the tubing 106. The vent cap luer lock 210 may have a female tapered fitting 212 that receives the male tapered fitting 202 of the tubing luer lock 200 in a manner that generally forms a seal with the male tapered fitting 202. The vent cap luer lock 210 may further have a male threaded interface 214 that mates with the female threaded interface 204 of the tubing luer lock 200 such that the vent cap luer lock 210 can be rotated into threaded engagement with the tubing luer lock 200.

The distal end 162 of the vent cap 110 may have a vent designed to be substantially permeable to air. This means that the vent permits passage of air therethrough at a flow rate sufficient to release all of the air from the intravenous delivery system 100 within a few minutes. Further, the vent may be designed to be substantially impermeable to liquids. This does not require that the vent provide a seal that is completely impervious to liquid passage, but rather, that the vent restricts liquid flow sufficient that, within a few minutes, only a relatively small percentage (for example, less than 2%) of the liquid within the intravenous delivery system 100 is able to escape.

As shown in FIG. 2, the vent may take the form of a hydrophobic membrane 220, which may be ultrasonically welded or otherwise attached to the remainder of the vent cap 110. The hydrophobic membrane 220 may generally repel the liquid 122, which may tend to cause the liquid 122 to remain displaced from the hydrophobic membrane 220, as shown, if there is any air present in the vent cap 110. Generally, air within the vent cap 110 may readily move to the hydrophobic membrane 220, but if the column of liquid 122 stops moving with air still within the air-carrying portion 190 of the second end 142 of the tubing 106, such air may remain lodged in the air-carrying portion 190. Thus, the vent cap 110 may be designed to receive a volume of liquid 122 at least equal to the volume of the air-carrying portion 190, as will be set forth in greater detail below.

Notably, the hydrophobic membrane 220 is only one example of many different vents that may be used within the scope of the present disclosure. Other structures (not shown) may be used in addition to or in the alternative to the hydrophobic membrane 220. Such structures include, but are not limited to, a hydrophilic filter, a perforated cap, and a cap with one or more tortuous passageways. A hydrophilic filter may have passageways that permit air to flow therethrough, but may resist leakage of liquid due to attraction of the liquid 122 to the hydrophilic filter, and the formation of a liquid barrier that may therefore occur along the surface of the hydrophilic filter. A perforated cap may have a plurality of apertures, each of which is small enough to resist egress of the liquid 122 therethrough (due to surface tension effects), but large enough to permit passage of air therethrough. In a cap with one or more tortuous passageways the each passageway may be narrow, and may follow a lengthy and/or curved pathway that resists outflow of the liquid 122 due to surface tension effects and/or the head loss that occurs along the length of the passageway, while still permitting air to escape.

Returning to the embodiment of FIG. 2, the vent cap 110 may have a chamber wall 230 that extends between the proximal end 160 and the distal end 162 of the vent cap 110. The chamber wall 230 may define an exterior wall of the vent cap 110, and may also define a chamber 232 within the vent cap 110. As embodied in FIG. 2, the chamber wall 230 may have a generally tubular shape, with some optional variations in diameter.

These variations in diameter may include a proximal flare 234 at which the chamber wall 230 joins the female tapered fitting 212 of the vent cap luer lock 210. At the proximal flare 234, the exterior of the diameter of the vent cap 110 may increase abruptly along the distal direction, i.e., from the proximal end 160 of the vent cap 110 to the main portion of the chamber wall 230. The proximal flare 234 may help to define the chamber 232 such that the chamber 232 has a volume sufficient to enable passage of substantially all of the liquid 122 from the air-carrying portion 190 into the chamber 232, as the priming of the intravenous delivery system 100 is completed and the leading edge of the liquid 122 advances from the distal end of the air-carrying portion 190 into the chamber 232.

More specifically, the chamber 232 may have a generally cylindrical shape defined within the generally tubular shape of the chamber wall 230. The chamber 232 may have a length 242 extending from the proximal flare 234 to the hydrophobic membrane 220, and diameter, which may be an interior diameter 244 of the chamber wall 230. The chamber 232 may not have a precisely cylindrical shape; however, the volume of the chamber 232 may be approximated by the formula $V_c=\pi r_c^2 l_c$, where $l_c$ is the length 242 of the chamber 232, and $r_c$ is the radius of the chamber 232, which is half of the interior diameter 244 of the chamber 232.

The dimensions of the chamber 232 may be determined by setting the volume $V_c$ of the chamber 232 equal to the volume $V_t$ of the air-carrying portion 190 of the tubing 106. Thus, the equation $\pi r_c^2 l_c = \pi r_t^2 l_t$ may be used to determine the dimensions of the chamber 232. For example, given the exemplary dimensions of the air-carrying portion 190, as set forth above, $r_t$ may be about 1.4 millimeters, or 0.0014 meters, and $l_t$ may be about 4 inches, or about 0.1016 meters. If the interior diameter 244 of the chamber 232 is to be 10 millimeters, the radius $r_c$ of the chamber 232 will be about 5 millimeters, or about 0.005 meters. Solving the equation above for $l_c$ provides that the length 242 of the chamber 232 should be about 8 millimeters, or 0.008 meters. In some embodiments, the length 242 of the chamber 232 may range from 5 millimeters to 10 millimeters, or more specifically, from 6.5 millimeters to 9 millimeters.

The variations in diameter of the chamber wall 230 may also include a distal flare 236. At the distal flare 236, the exterior diameter of the vent cap 110 may again increase abruptly along the distal direction, i.e., from the main portion of the chamber wall 230 to the distal end 162 of the vent cap 110. The distal flare 236 may define a seat on which the hydrophobic membrane 220 may be secured, for example, via ultrasonic welding, as indicated previously. The vent cap 110 may be oriented upright, so that the hydrophobic membrane 220 is above the chamber 232. In this manner, air 250 within the chamber 232 may float toward the hydrophobic membrane 220, in the direction shown by the arrow 252, and may exit the vent cap 110 through the hydrophobic membrane 220.

In some alternative embodiments (not shown), a vent cap may have a chamber that is configured to facilitate and/or expedite air flow to the vent. For example, in place of a cylindrical shape, such a chamber may have different geometry that helps to wick the water away and/or allow the air to coalesce. Additionally or alternatively, an absorbent material such as a hydrophilic fibrous mat may be positioned within the chamber to facilitate such wicking and/or coalescing.

The intravenous delivery system 100 may be prepared for use according to a variety of methods. One example of the use of a system, such as the intravenous delivery system 100, will be described in greater detail in connection with FIG. 3, as follows.

Figure 3:
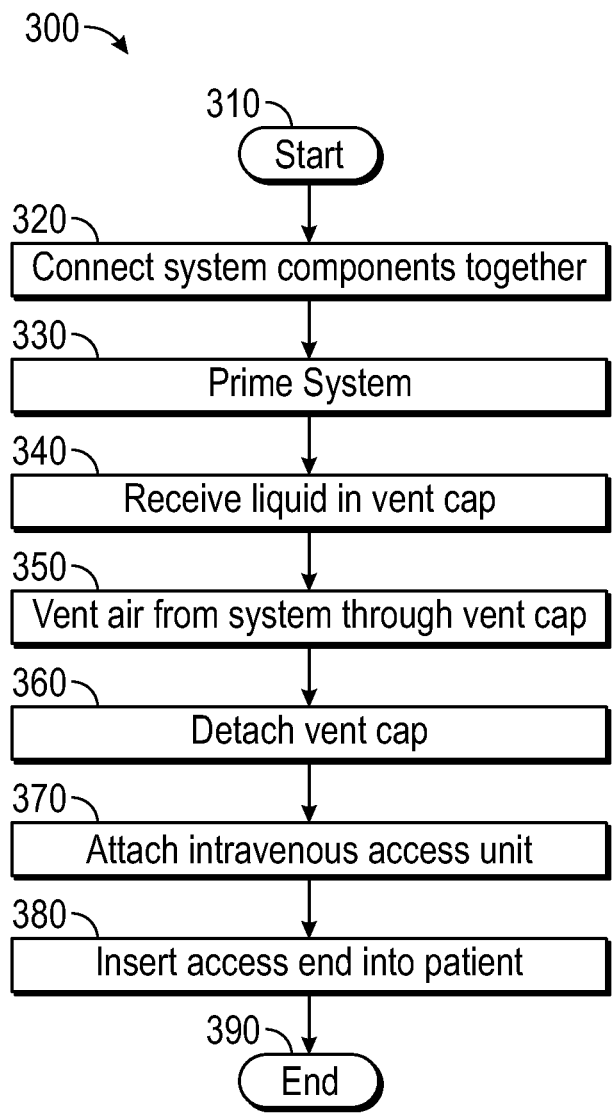
FIG. 3 is a flowchart diagram illustrating a method of preparing an intravenous delivery system for use, according to one embodiment.

Referring to FIG. 3, a flowchart diagram illustrates a method 300 of preparing an intravenous delivery system for use, according to one embodiment. The method 300 will be described with reference to the intravenous delivery system 100 of FIGS. 1 and 2. However, those of skill in the art will recognize that the method 300 may be carried out with different intravenous delivery systems. Similarly, the intravenous delivery system 100 may be prepared for use through the use of methods other than that of FIG. 3.

The method 300 may start 310 with a step 320 in which the various components of the intravenous delivery system 100 are connected together, except for the intravenous access unit 112. Some of the components of the intravenous delivery system 100, such as the tubing 106 and the vent cap 110, may be packaged, sold and/or provided to the end user in a condition in which they are already connected together. The step 320 may only include interconnection of components of the intravenous delivery system 100 that have not already been connected together.

In a step 330, the intravenous delivery system 100 may be primed. As indicate previously, this may be done by simply allowing the liquid 122 to flow through the tubing 106 to the vent cap 110 via gravity, or by squeezing or otherwise pressuring the drip unit 104.

In a step 340, the liquid 122 may be received in the vent cap 110. As mentioned previously, the liquid 122 disposed within the air-carrying portion 190 when the liquid 122 has advanced to the distal end of the air-carrying portion 190 may be received within the chamber 232 of the vent cap 110. The chamber 232 of the vent cap 110 may be deliberately sized to accomplish this.

In a step 350, the air 250 may be vented from the intravenous delivery system 100. This may entail permitting passage of the air 250 to the top of the chamber 232, and through the hydrophobic membrane 220 of the vent cap 110. The intravenous delivery system 100 may now be ready for attachment and use of the intravenous access unit 112.

In a step 360, the vent cap 110 may be detached from the second end 142 of the tubing 106. This may entail detaching the vent cap luer lock 210 of the vent cap 110 from the tubing luer lock 200 of the second end 142 of the tubing 106.

In a step 370, the intravenous access unit 112 may be attached to the second end 142 of the tubing 106. The first end 170 of the intravenous access unit 112 may have a luer lock that mates with the tubing luer lock 200 of the second end 142 of the tubing 106. Thus, performance of this step may entail mating the luer lock of the first end 170 of the intravenous access unit 112 with the tubing luer lock 200 of the second end 142 of the tubing 106.

The intravenous delivery system 100 is only one of many different possible embodiments of an intravenous delivery system, according to the present disclosure. In alternative embodiments, various different vent cap configurations may be provided. Such alternative vent cap configurations may advantageously be designed to retain the liquid 122 within the chamber 232 after detachment of the second end 142 of the tubing 106, without requiring the presence of a valve as part of the vent cap 110. Two such alternative embodiments will be shown and described in connection with FIGS. 4 and 5, as follows.

Figure 4:
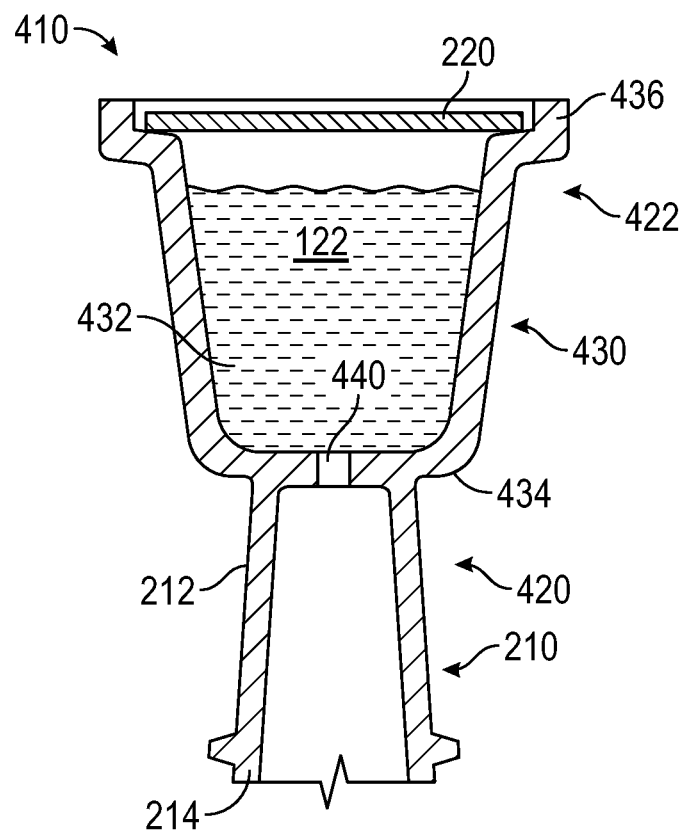
FIG. 4 is a front elevation, section view of a vent cap according to one alternative embodiment.

Referring to FIG. 4, a front elevation, section view illustrates a vent cap 410 according to one alternative embodiment. The vent cap 410 may be a component of an intravenous delivery system like that of FIG. 1, and may thus be detachably coupled to tubing, such as the distal end 162 of the tubing 106 of FIG. 1. The vent cap 410 may have a proximal end 420 and a distal end 422. The vent cap 410 may have some features similar to the corresponding features of the vent cap 110, such as the vent cap luer lock 210 and the hydrophobic membrane 220.

Like the vent cap 110, the vent cap 410 may have a chamber wall 430 with a generally tubular shape that defines a chamber 432. The chamber wall 430 may have a proximal flare 434 and a distal flare 436 that cooperate to define the extents of the chamber 432 and provide a seat for the hydrophobic membrane 220. Like the chamber 232, the chamber 432 may have a volume selected to enable the chamber 432 to receive substantially all of the liquid 122 contained in the air-carrying portion 190 of the distal end 162 of the tubing 106, as the priming process reaches completion. This is likely the liquid 122 within which entrained air, if present, will reside. The air may be vented from the vent cap 410 through the hydrophobic membrane 220, as in the vent cap 110.

The vent cap 410 may be designed such that, after detachment of the vent cap 410 from the distal end 162 of the tubing 106, the vent cap 410 retains substantially all of the liquid 122 contained within the chamber 432, or in other words, substantially preventing flow of the liquid 122 out of the vent cap 410 through the orifice 440. In this application, retaining "substantially all" of the liquid and "substantially preventing" flow of the liquid 122 through the orifice 440 do not require retention of 100% of the liquid 122. Rather, these phrases relate to retention enough of the liquid 122 that after detachment of the vent cap 410 from the distal end 162, leakage of liquid 122 from within the chamber 432 is limited to a few drops of the liquid 122.

The phrase "without requiring the presence of a valve within the vent cap" does not mean that there is no valve within a vent cap, but rather means that a function, such as prevention of outflow of the liquid 122 from the vent cap, does not require the use of a valve. A "valve" is device having at least one movable member that enables the valve to move between an open state, in which fluid flow through the valve is permitted, and a closed state, in which fluid flow through the valve is more restricted than in the open state.

In the embodiment of FIG. 4, this may be accomplished through the use of an orifice 440, which may be formed in the chamber wall 430 between the chamber 432 and the vent cap luer lock 210. The orifice 440 may have a size selected such that substantially all of the liquid 122 is retained in the chamber 432 after detachment of the vent cap 410 from the distal end 162 of the tubing 106. More specifically, the surface tension at the boundary between the liquid 122 and the ambient air proximate the orifice 440 may be sufficient to counteract any forces tending to remove the liquid 122 from the chamber 432 through the orifice 440. Such forces may include gravity, as the vent cap 410 will likely be positioned with the orifice 440 below the liquid 122 in the chamber 432, as illustrated in FIG. 4, at the time it is detached from the distal end 162 of the tubing 106.

Retention of the liquid 122 within the chamber 432 after detachment of the vent cap 410 from the tubing 106 may beneficially minimize spillage of the liquid 122, and may help keep the clinical environment sterile. The orifice 440 represents only one mechanism for accomplishing this without requiring the presence of an internal valve. Another example will be shown and described in connection with FIG. 5.

Figure 5:
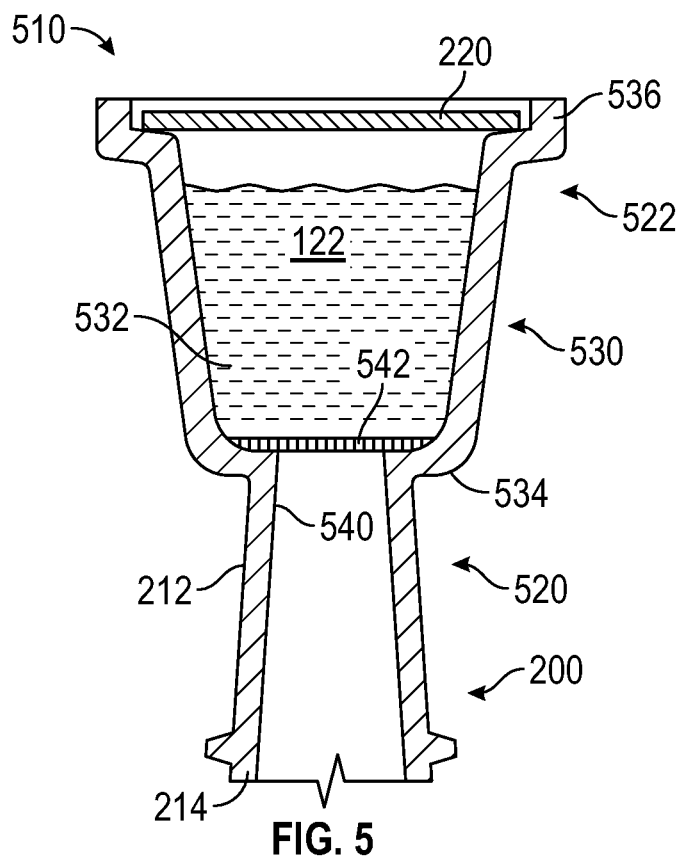
FIG. 5 is a front elevation, section view of a vent cap according to another alternative embodiment.

Referring to FIG. 5, a front elevation, section view illustrates a vent cap 510 according to another alternative embodiment. The vent cap 510 may be a component of an intravenous delivery system like that of FIG. 1, and may thus be detachably coupled to tubing, such as the distal end 162 of the tubing 106 of FIG. 1. The vent cap 510 may have a proximal end 520 and a distal end 522. The vent cap 510 may have some features similar to the corresponding features of the vent cap 110 and the vent cap 410, such as the vent cap luer lock 210 and the hydrophobic membrane 220.

Like the vent cap 110 and the vent cap 410, the vent cap 510 may have a chamber wall 530 with a generally tubular shape that defines a chamber 532. The chamber wall 530 may have a proximal flare 534 and a distal flare 536 that cooperate to define the extents of the chamber 532 and provide a seat for the hydrophobic membrane 220. Like the chamber 232 and the chamber 432, the chamber 532 may have a volume selected to enable the chamber 532 to receive substantially all of the liquid 122 contained in the air-carrying portion 190 of the distal end 162 of the tubing 106, as the priming process reaches completion. This is likely the liquid 122 within which entrained air, if present, will reside.

The air may be vented from the vent cap 510 through the hydrophobic membrane 220, as in the vent cap 110 and the vent cap 410.

Like the vent cap 410, the vent cap 510 may be designed such that, after detachment of the vent cap 510 from the distal end 162 of the tubing 106, the vent cap 510 retains substantially all of the liquid 122 contained within the chamber 532. The vent cap 510 may have an orifice 440 formed in the chamber wall 530 between the chamber 532 and the vent cap luer lock 210. The orifice 540 need not have any particular size. Rather, retention of the liquid 122 within the chamber 532 may be accomplished through the use of a hydrophilic membrane 542 that covers the orifice 540 and defines a boundary between the chamber 532 and the vent cap luer lock 210. Due to the hydrophilic composition of the hydrophilic membrane 542, the liquid 122 may adhere to the hydrophilic membrane 542. This adherence may be sufficient to counteract forces, such as gravity, tending to cause the liquid 122 to exit the chamber 532 through the orifice 540.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

I claim:

1. An intravenous delivery system, comprising:
    a liquid source containing a liquid;
    tubing, comprising:
        a first end connectable to the liquid source to receive the liquid from the liquid source; and
        a second end; and
    a vent cap, comprising:
        a proximal end connectable to the second end of the tubing to receive the liquid from the tubing;
        a distal end comprising a hydrophobic membrane that is substantially impermeable to the liquid and substantially permeable to air; and
        a chamber formed by a chamber wall, the chamber wall comprising a proximal flare that extends outwardly away from a longitudinal axis of the vent cap to increase a volume of the chamber configured to receive the liquid from the proximal end, wherein the proximal flare is positioned to contact the liquid from the proximal end, wherein the chamber is in communication with the hydrophobic membrane to facilitate passage of air from the liquid out of the vent cap through the hydrophobic membrane,
        wherein when the proximal end of the vent cap is connected to the second end of the tubing, the chamber is configured to hold a first volume of the liquid equal to a second volume of the liquid configured to be held in 2 inches to 15 inches of the tubing, wherein the hydrophobic membrane is positioned adjacent to the chamber;
        a luer lock extending from the proximal flare and having threading on an outer surface of the luer lock, wherein the luer lock comprises a female taper, wherein an inner diameter of a portion of the chamber distal the proximal flare is greater than an inner diameter of the luer lock; and a drip unit comprising a drip chamber, wherein the drip unit is connected to the liquid source to receive drops of the liquid from the liquid source within the drip chamber, wherein the drip unit is connected to the first end of the tubing to supply the liquid to the tubing via gravity feed.

2. The intravenous delivery system of claim 1, wherein the first volume is determined by the equation $V=\pi r^2 l$, where V is the first volume, r is a radius of an interior of the tubing, and l is a length of tubing within a range of 2 inches to 15 inches.

3. The intravenous delivery system of claim 2, wherein the first volume and the second volume are each within a range of 0.3 milliliters to 2.7 milliliters.

4. The intravenous delivery system of claim 1, wherein the chamber wall has a generally tubular shape comprising an interior diameter within a range of 7 millimeters to 15 millimeters.

5. The intravenous delivery system of claim 1, wherein the chamber wall has a generally tubular shape comprising a length within a range of 5 millimeters to 15 millimeters.

6. The intravenous delivery system of claim 1, wherein the tubing comprises a tubing luer lock that mates with the vent cap luer lock.

7. The intravenous delivery system of claim 6, wherein the chamber wall has a cross-sectional area larger than a largest cross-sectional area of the vent cap luer lock.

8. The intravenous delivery system of claim 1, wherein the chamber wall is shaped to define an orifice adjacent to the chamber, wherein the orifice is sized such that, after detachment of the vent cap from the tubing, the orifice prevents flow of liquid out of the cap through the orifice.

9. The intravenous delivery system of claim 1, further comprising an intravenous access unit connectable to the second end of the tubing to deliver the liquid intravenously to a patient.

\* \* \* \* \*